United States Patent
Bhaskaran et al.

(10) Patent No.: US 9,139,608 B2
(45) Date of Patent: Sep. 22, 2015

(54) **METHOD FOR PREPARATION OF HIGHLY PURE ASIATICOSIDE COMPOSITION FROM *CENTELLA ASIATICA* AND A METHOD OF USE THEREOF**

(75) Inventors: Sunil Bhaskaran, Pune (IN); Mohan Vishwaraman, Pune (IN)

(73) Assignee: Indus Biotech Private Limited, Pune (IN)

( * ) Notice: Subject to any disclaimer, the term of this patent is extended or adjusted under 35 U.S.C. 154(b) by 27 days.

(21) Appl. No.: 13/702,834

(22) PCT Filed: Aug. 31, 2010

(86) PCT No.: PCT/IN2010/000575
§ 371 (c)(1),
(2), (4) Date: Dec. 7, 2012

(87) PCT Pub. No.: WO2011/154966
PCT Pub. Date: Dec. 15, 2011

(65) Prior Publication Data
US 2013/0089605 A1    Apr. 11, 2013

(30) Foreign Application Priority Data
Jun. 10, 2010 (IN) .......................... 1760/MUM/2010

(51) Int. Cl.
*C07H 1/08* (2006.01)
*A61K 31/7028* (2006.01)
*A61K 31/702* (2006.01)
*A61K 36/23* (2006.01)

(52) U.S. Cl.
CPC ................ *C07H 1/08* (2013.01); *A61K 31/702* (2013.01); *A61K 31/7028* (2013.01); *A61K 36/23* (2013.01)

(58) Field of Classification Search
CPC .............................. C07H 1/08; A61K 31/7028
USPC ..................... 424/455, 400; 514/25; 536/18.1
See application file for complete search history.

(56) References Cited

U.S. PATENT DOCUMENTS

| | | | |
|---|---|---|---|
| 6,207,164 B1 * | 3/2001 | Kreuter et al. | ................. 424/725 |
| 6,417,349 B1 | 7/2002 | Kim et al. | |
| 2003/0039706 A1 * | 2/2003 | Hirose et al. | ................. 424/725 |
| 2004/0097463 A1 | 5/2004 | Oh et al. | |
| 2006/0106206 A1 | 5/2006 | Loiseau et al. | |
| 2006/0177516 A1 | 8/2006 | Merizzi | |
| 2007/0237841 A1 * | 10/2007 | Wu et al. | ...................... 424/725 |
| 2008/0194499 A1 | 8/2008 | Bhaskaran | |
| 2009/0060985 A1 | 3/2009 | Wu et al. | |

FOREIGN PATENT DOCUMENTS

| | | |
|---|---|---|
| CN | 1439376 A | 9/2003 |
| CN | 1520824 A | 8/2004 |
| CN | 101129393 A | 2/2008 |
| EP | 1925310 A1 | 5/2008 |

OTHER PUBLICATIONS

Asiaticoside Product Information: retrieved from internet: https://www.caymanchem.com/.../11819.pdf. Retrieved on Jul. 21, 2014.*
Cheng et al., Effects of *Centella asiatica* on ethanol induced gastric mucosal lesions in rats, Life Sciences, 2000, pp. 2647-2653, vol. 67.
Cheng et al., The healing effects of *Centella* extract and asiaticoside on acetic acid induced gastric ulcers in rats, Life Sciences, 2004, pp. 2237-2249, vol. 74.

* cited by examiner

*Primary Examiner* — Ernst V Arnold
*Assistant Examiner* — Hong Yu
(74) *Attorney, Agent, or Firm* — The Webb Law Firm

(57) ABSTRACT

Disclosed is a commercially viable asiaticoside composition having at least 99% purity that is derived from plant *Centella asiatica* and a manufacturing process thereof. Also disclosed is a method and the models for oral administration of therapeutically effective amounts of the asiaticoside composition for treatment of Inflammatory Bowel Diseases such as Ulcerative colitis, Crohn's disease and associated complications of inflammatory bowel diseases such as hemorrhoids, anal fissures, fistulas. Also disclosed is a method and model for oral administration of therapeutically effective amounts of the asiaticoside composition for treatment of *Helicobacter Pylori*, as well as a method and the models for oral administration of therapeutically effective amounts of the asiaticoside composition for prevention of colon cancer, gastric diseases and gastric carcinoma.

14 Claims, No Drawings

METHOD FOR PREPARATION OF HIGHLY PURE ASIATICOSIDE COMPOSITION FROM CENTELLA ASIATICA AND A METHOD OF USE THEREOF

FIELD OF THE INVENTION

This invention relates to an extract of asiaticoside from *Centella Asiatica*, and more particularly, use thereof for management of inflammatory bowel diseases, treatment of *Helicobacter Pylori*, prevention of gastric diseases and gastric carcinoma.

BACKGROUND OF THE INVENTION

Asiaticoside extracted from *Centella asiatica* is a commercially available analytical reference standard material with companies such as, for example, Yick-Vic Company having attributed Asiaticoaside purity of 92.8% by HPLC, Tauto Biotech Company having attributed Asiaticoaside purity around 97% by HPLC, and Baoji herbest Biotech Company having Asiaticoaside assay more than 98%. However, these products are specifically adapted to be used as a reference standard for research purposes in the research laboratories and not found to be an extract of plant *centella asiatica*. These asiaticoside products are not commercially viable to be used as a pharmaceutical composition.

The processes adapted for preparation of asiaticoside from *centella asiatica* claim purity ranging between 50%-97% in the prior art. For example, US Publication No. 2008/0194499 teaches pharmaceutical pentacyclic terpenoid glycosides that include asiaticoside composition ranging between 15-50%. Also, US Publication No. 2006/0177516 discloses a terpenic mixture having asiaticoside composition around 40%. Moreover, U.S. Pat. No. 6,417,349 provides a *centella asiatica* extract having range 4:6 to 6:4 to constitute 97% or more of the extract. In addition, Chinese Patent No. CN 1520824 discloses an extraction and separation method for asiaticoside that has purity 92.8%. However, none of the prior art has attempted exclusive extraction of highly pure asiaticoside from *centella asiatica*.

The traditional use of *Centella Asiatica* or Asiaticoside includes promoting wound healing, treatment of skin diseases, skin disorders and chronic inflammatory diseases. For example, Chinese patent no. CN 101129393 discloses the use of asiaticoside liquid in wound healing. In addition, US Publication No. 2009/0060985 teaches uses of *centella asiatica* urban extract as a drug substance for treatment of skin disorders. There are few attempts seen in the art wherein the asiaticoside or *centella asiatica* is employed for non-traditional uses. For example, US Publication No. 2008/0194499 teaches the use of terpenoid glycosides, preferably asiaticoside and madecassoside optionally along with excipients, for management of depression. Also, US Publication No. 2006/0177516 provides a food supplement that shows uses of Asiaticoside for treatment of anemia conditions.

However, the use of asiaticoside or *centella asiatica* for management of diseases related to gastrointestinal tract such as inflammatory bowel disease and *helicobacter pylori* is relatively unknown. There are few attempts seen in the art wherein the asiaticoside is used for treatment of liver diseases. For example, Chinese patent nos. CN1439376 and CN 1520824 disclose the use of asiaticoside for preventing and treating fibrosis of liver. In addition, US Publication No. 2004/0097463 discloses the use of asiaticoside for treatment of cancer associated with liver, colon and pancreas. In addition, Cheng et al., 2004, ("The healing effects of *Centella* extract and asiaticoside on acetic acid induced gastric ulcers in rats", Life Sciences, vol. 74, pp. 2237-2249) discusses the healing effects of *Centella asiatica* water extract on acetic acid induced gastric ulcers in rats. Also, Cheng et al., 2000, ("Effects of *Centella asiatica* on ethanol induced gastric mucosal lesions in rats", Life Sciences, vol. 67, pp. 2647-2653) teaches preventive effect of water extract of *Centella asiatica* on ex-vivo experiments of ethanol induced gastric mucosal lesions. However, the gastric ulcers stated in the art are restricted to chemical or drug induced ulceration models. Moreover, these models specifically create a lesion by local application of an irritant (acetic acid) in the stomach which may not necessarily address the diseases of the colon such as inflammatory bowel diseases. Moreover, the asiaticoside products in the art claim for treatment of ulcers, but fail to specify the use of asiaticoside for prevention of ulcers.

Inflammatory Bowel Disease is characterized by intractable, chronic inflammatory conditions such as Ulcerative Colitis and Crohn's Disease which display distressing symptoms of abdominal pain, diarrhea, vomiting, hematochezia (blood in stools), reduced appetite, weight loss, fever and various associated complications such as anal fissures, fistulas, perirectal abscess, hemorrhoids, for example. Ulcerative Colitis and Crohn's Disease are usually assessed by disease activity index, which includes stool frequency, presence of blood in stool, endoscopic appearance, and physician's global assessment. Persistence of above conditions leads to chronic inflammation and subsequently becomes the causative factors for development of colonic cancers. The existing methods of treatment for inflammatory bowel diseases include the reduction of abdominal pain, diarrhea, fatigue, anemia, nutrient deficiencies, mucosal inflammation, extra intestinal manifestations, hospitalizations, operations, and complications, such as abscesses, fistulae, infections, and malignancy.

The treatment of inflammatory bowel diseases consists of oral administration of sulfasalazine, immunosupressants and corticosteroids. Normally, Sulfasalazine is a preferred first line treatment for mild to moderate Ulcerative Colitis and Crohn's Disease. However, the side effects such as drug intolerance, impaired folic acid absorption, renal adverse effects make Sulfasalazine undesirable for inflammatory bowel disease treatment. Further, the availability of Sulfasalazine at the colon is limited due to its absorption in the stomach and subsequent excretion in the urine. Ulcerative Colitis and Crohn's Disease, in acute conditions, require treatment with corticosteroids but these drugs cannot prevent remission. Long term use of corticosteroids is associated with skin thinning, susceptibility to laceration, weight gain, increase in blood pressure, diabetes and related adverse conditions. Immunosuppressants are effective in long term treatment of Ulcerative Colitis and Crohn's Disease. These drugs also have significant adverse reactions such as bone marrow suppression, lymphomas (in renal transplant patients), skin cancer and pancreatitis. The inflammatory bowel disease require surgery in severe cases, such as bowel resection, stricture plasty or a temporary or permanent colostomy or ileostomy which involves use of general anesthesia and complications of post operative recovery. Ulceration of gastrointestinal tract by mucosal damage is an associated complication of inflammatory bowel disease. The chronic nature of inflammatory bowel disease and associated inflammatory diseases require long term management therapy. Current methods of treatment of inflammatory bowel disease have limitations of adverse side-effects on sustained treatment and high risk of remission of the disease.

The inflammations that are induced by pathogenic bacteria such as *helicobacter pylori* help facilitate to aggravate the symptoms of inflammatory bowel diseases. Moreover, the environmental factors such as stress, food and alcohol consumption amplify the activity of *helicobacter pylori*. The World Health Organization (WHO) has categorized *helicobacter pylori* as group-I carcinogen for promoting gastric carcinoma. The *helicobacter pylori* infection triggers chronic inflammatory reaction that damages epithelial cell followed by induction of gastric atrophy that eventually leads to gastric carcinoma. The treatment of gastric carcinoma or gastric cancer has highly fatal treatment options such as, for example, surgical removal of cancerous tissue by gastrectomy, removal of part/total stomach, chemotherapy, radiation and chemo radiation. However, these treatments have substantially high side-effects that lead poor quality of life to the patients. Also, these treatments do no assure complete recovery as there is a high probability of recurrence of the carcinoma. Timely diagnosis and treatment for eradication of *helicobacter pylori* from infected gastric mucosa may greatly reduce the risk of gastric carcinoma. A user may appreciate an effective means for eradication of *helicobacter pylori* infection, which can indirectly help in prevention of gastric carcinoma induced by *helicobacter pylori* infection.

A commercially viable method for extraction of asiaticoside from *centella asiatica* is needed that has a very high purity to be effectively used as a pharmaceutical composition. An asiaticoside composition is further needed that provides a kinder and gentler method for effective long-term management of inflammatory bowel disease along with *helicobacter pylori*. An asiaticoside composition is further needed that prevents gastric diseases and colon cancers that are induced due to inflammatory bowel diseases. An asiaticoside composition is further needed for effective eradication of the *helicobacter pylori* infection that prevents a gastric carcinoma.

SUMMARY OF THE INVENTION

The main object of the present invention is to provide a method or process of preparation of a pharmaceutical composition of asiaticoside derived from *Centella Asiatica* that has at least 99% purity.

Another object of the present invention is to provide the pharmaceutical composition of asiaticoside, optionally along with acceptable pharmaceutical excipients, for treatment of Inflammatory Bowel Diseases such as Ulcerative Colitis, Crohn's Disease.

Yet another object of the present invention is to provide the pharmaceutical composition of asiaticoside, optionally along with acceptable pharmaceutical excipients, for treatment of associated complications of inflammatory bowel diseases such as but not limited to hemorrhoids, anal fissures, fistulas.

Still another object of the present invention is to provide the pharmaceutical composition of asiaticoside, optionally along with acceptable pharmaceutical excipients, for prevention of colon cancer.

Still another object of the present invention is to use a pharmaceutical composition of asiaticoside optionally along with acceptable pharmaceutical excipients, for treatment of *Helicobacter Pylori*.

Still another object of the present invention is to use a pharmaceutical composition of asiaticoside optionally along with acceptable pharmaceutical excipients, for prevention of gastric diseases and gastric carcinoma.

STATEMENT OF THE INVENTION

The present invention discloses a commercially viable pharmaceutical grade asiaticoside composition extracted from a plant material *centella asiatica* having at least 99% purity. The present invention discloses an in-vivo method of the treatment in humans and animals wherein the method of treatment comprises oral administration of the asiaticoside composition adapted for treatment of Inflammatory Bowel Diseases, treatment of hemorrhoids, anal fissures, and fistulas, prevention of a colon ulcer and cancer, treatment of eradication of a *helicobacter pylori* infection, prevention of gastric diseases, and prevention of a gastric carcinoma.

DETAILED DESCRIPTION OF THE INVENTION

In the context of the present invention, Asiaticoside compound disclosed herein has the following structure:
Asiaticoside:

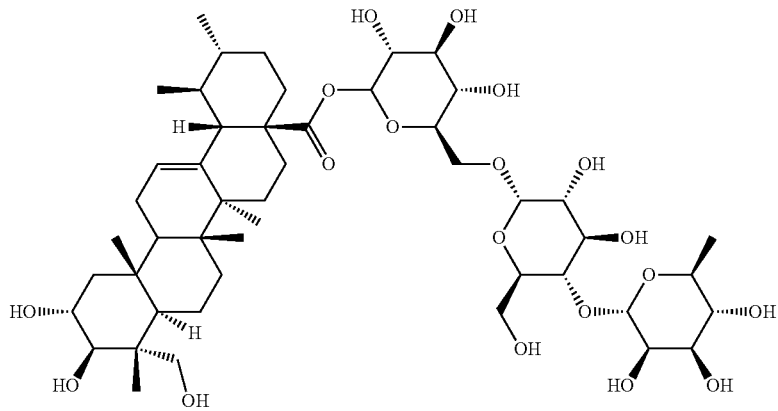 [SMILES: C[C@H]1[C@H](C)CC[C@]2(C(=O)OC3O[C@H](CO[C@H]4O[C@H](CO)[C@@H](O[C@@H]5O[C@@H](C)[C@H](O)[C@@H](O)[C@H]5O)[C@H](O)[C@H]4O)[C@@H](O)[C@H](O)[C@H]3O)CC[C@]3(C)C(=CCC4[C@@]5(C)C[C@@H](O)[C@H](O)[C@@](C)(CO)[C@@H]5CC[C@]43C)[C@H]12]

In a preferred embodiment, the present invention provides a highly pure composition of asiaticoside having at least 99% purity and a process of manufacturing thereof. Asiaticoside of the present invention has a molecular formula $C_{48}H_{78}O_{19}$. Asiaticoside is obtained from plant source *Centella asiatica* in this one preferred embodiment, however, it is understood that Asiaticoside can be obtained from animal sources in other alternative embodiments of the present invention.

In particular, the present invention provides a method or process for preparation of a composition having 99% or more of asiaticoside, wherein said process comprising steps of:
- a) Pulverizing plant material of *Centella asiatica*
- b) Treating pulverized material with a first solvent to remove fatty substances, chlorophyll and other colorants;
- c) Extracting the bioactive molecules using a second solvent;
- d) Distilling extract to remove solvents and form a paste;
- e) Dissolving distilled paste in a third solvent to obtain a solution;
- f) Extracting with a third solvent to remove acidic impurities;
- g) Passing purified extract through adsorbents to get a clear solution;
- h) Eluting the resin bed with an alcoholic solvent to obtain a solvent elute;
- i) Vacuum concentration of the solvent elute to obtain a powder; and
- j) Aqueous-alcohol dissolution of the powder and crystallization to obtain asiaticoside composition that has at least 99% HPLC purity.

The detailed method or process for preparation of the 99% or more of asiaticoside composition is described hereinafter:

In accordance with the present invention, dry leaves of *Centella asiatica* including stems are pulverized to 40 mesh size. The pulverized material is packed in an extractor having perforated plates at the top and bottom of the vessel that is fitted with filter cloths.

In next step, a first solvent is circulated through the extractor in a counter current manner at temperature ranging between 20° C. to 30° C., most preferably at 30° C., for a time period ranging between 8 hrs to 24 hrs, most preferably for 12 hrs. In this one preferred embodiment the first solvent used is petroleum ether having a boiling range of 60° C. to 80° C. However, it is understood that the first solvent can be selected from a group comprising aliphatic compounds, ketones, alcohols, nitrites, esters, ether and mixtures of one or more thereof in other embodiment of the present invention. In next step, Chlorophyll and other lipids are removed from the extract and the mass is allowed dry free of solvent.

In next step, the dried mass is extracted in a counter current manner using a second solvent. The second solvent in this one preferred embodiment is a combination of aliphatic alcohols that has Carbon atom ranging from 1 to 4, both straight chain and branched chain alcohols, in combination with or without water. In other alternative embodiments of the present invention, the second solvent can be selected from a methyl alcohol, an ethyl alcohol, a propyl alcohol, an isopropyl alcohol and a butyl alcohol—either alone or in combination with water in a ratio ranging from 60% to 99%.

In next step, the clear extract is distilled under reduced pressure to evaporate solvent and to form a paste. In next step, the paste is dissolved in demineralized water and filtered clear of insolubles. In next step, the clear water layer is extracted repeatedly and washed with a third solvent to get rid of acidic material and to obtain a clear aqueous extract. The third solvent in this one preferred embodiment is methyl isobutyl ketone. In still another embodiment of the present invention, the solvent can be selected from a group comprising hexane and petroleum ether.

In next step, the clear aqueous extract layer is adapted to be passed through a bed of adsorbent grade resin and washed to get rid of all the colors and contaminants out of the bed with 5 volumes or more preferably 8 volumes of deionised water.

In next step, the water washed bed is eluted with an alcoholic solvent having carbon atom ranging from C-1 to C-4, preferably methanol or isopropyl alcohol or a mixture of the said alcohols. The eluted solvent is collected and the bed repeatedly washed to get all the centellosaponins out of the bed.

In next step, the solvent elute is concentrated under vacuum at low temperature preferably between 50° C. to 65° C. to a powder. The powder is redissolved in aqueous alcohol to form a solution. The aqueous alcohol used in this one preferred embodiment is methyl alcohol. However, it is understood that aqueous alcohol can be selected from a group of ethyl, propyl alcohol or isopropyl alcohol—either alone or in combination with water in ratios ranging from 50% to 99% of alcohol.

In next step, the solution is cooled to less than 0° C., preferably at −15° C. or below to crystallize the asiaticoside. In next step, the pure asiaticoside crystals obtained is filtered off and washed with cold water until free of salts and dried under vacuum to get free flowing powder that can be analyzed for its purity using HPLC for assay.

A summary of the most preferred process is as follows:
- a) Dry leaves of *Centella asiatica* including stems were pulverized to 40 mesh size.
- b) Pulverized material is packed in an extractor having perforated plates at top and bottom of the vessel having filter cloths.
- c) Petroleum ether having a boiling range of 60° C. to 80° C. is circulated in a counter current manner at temperature ranging between 20° C. to 30° C. preferably at 30° C. for a time period ranging between 8 hrs to 24 hrs preferably for 12 hrs.
- d) The resultant extract consisting of Chlorophyll and other lipids are removed and the mass allowed dry free of solvent.
- e) The dried mass is extracted again in a counter current manner using a combination of aliphatic alcohol solvents having Carbon atom ranging from 1 to 4 both straight chain and branched chain alcohols in combination with or without water. The said alcohols can be methyl, ethyl, propyl, isopropyl, butyl alcohol either alone or in combination with water in the ratio ranging from 60% to 99% of said alcohol.
- f) The clear extract is made into a paste by evaporating solvent by distillation under reduced pressure.
- g) The paste is dissolved in demineralized water and washed repeatedly with methyl isobutyl ketone.
- h) The clear aqueous extract is then passed through a bed of adsorbent grade resin and washed free of all the colors and contaminants out of the bed with 5 volumes or more preferably 8 volumes of deionised water.
- i) The water washed bed was eluted with an alcoholic solvent having carbon atom ranging from C-1 to C-4, preferably methanol or isopropyl alcohol or a mixture of the said alcohols.
- j) The eluted solvent was collected and the bed repeatedly washed to get all the centellosaponins out of the bed.
- k) The solvent elute was concentrated under vacuum at low temperature preferably between 50° C. to 65° C. to a powder.
- l) The powder is redissolved in aqueous alcohol in which the alcohol used is ethyl, methyl, propyl or isopropyl in combination or with water in ratios ranging from 50% to 99% of alcohol and cooled to less than 0° C. preferably at −15° C. or below to crystallize the asiaticoside.

m) The pure asiaticoside thus formed is filtered off and washed with cold water until free of salts and dried under vacuum to get free flowing powder.

n) The material thus isolated is analyzed for its purity in the following manner using HPLC for assay as well as impurities. HPLC method for analysis is as follows:

Column: 250 mm × 4.6 mm
Reverse phase C-18 particle size 5 μ
Wavelength of detector: 220 nm
Flowrate: 1.4 ml/min
Standard Used: Chromadex
Lot No 11030-291

| Time | Acetonitrile | Water |
|---|---|---|
| Initial | 75% | 25% |
| 30 mins | 45% | 55% |
| 40 mins | 75% | 25% |

In still another embodiment of the present invention, Asiaticoside composition is optionally usable along with acceptable pharmaceutical excipients selected from a group such as but not limited to granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents and spheronization agents.

In still another embodiment of the present invention, Asiaticoside composition can be formulated into various dosage forms selected from a group such as tablets, troches, lozenges, aqueous or oily suspensions, ointments, patches, gels, lotions, dentifrices, capsules, emulsions, creams, sprays, drops, dispersible powders or granules, emulsions in hard or soft gel capsules, syrups, elixirs, phytoceuticals, nutraceuticals and food stuffs, for example.

In still another embodiment of the present invention, composition is either a powder or liquid and has minimal side effects, wherein the composition is in a dosage range of 1-360 mg/kg in animals and 1-60 mg/kg in human beings. The asiaticoside composition adapted to be administered as a therapeutic or a prophylactic dose for effective treatment of a diseased site.

In the preferred embodiment, the present invention additionally provides an in-vivo method of treating Inflammatory Bowel Diseases (IBD hereinafter) such as Ulcerative Colitis (UC hereinafter), Crohn's Disease (CD hereinafter) and associated complications of hemorrhoids, anal fissures, fistulas, and prevention of colon cancer induced by the above conditions.

In the preferred embodiment, the present invention also provides an in-vivo method of treating *Helicobacter Pylori* (*H. Pylori* herein after). Moreover, the present invention also provides an in-vivo method of eradication of *H. Pylori* in NSAID induced ulcers.

In the preferred embodiment, the present invention also provides an in-vivo method of preventing gastric diseases and gastric carcinoma.

Accordingly, in the context of the present invention, the tests that are conducted to ascertain an anti-inflammatory activity, a healing activity, a method of use and an establishment of mode of action of the asiaticoside composition (test drug hereinafter) are described in detail hereinafter:

a) In a pharmacokinetic study, the test drug is administered and its bioavailability in blood and excretion in urine and feces are analyzed. It is observed that asiaticoside not absorbs into the blood, but excretes completely in the fecal matter in the unchanged form. This property of the test drug prompted further investigation for treating IBD and related diseases.

b) In trinitrobenzene sulfonic acid (TNBS) induced IBD model, the test drug on post treatment for 10 days after TNBS administration has significantly reduced colon weight and colon weight/length ratio. In addition, increased body weight, decreased ulcer index and myeloperoxidase activity in colon is seen. Also, the rectal bleeding is significantly reduced after $3^{rd}$ day of test drug administration.

c) In acetic acid induced IBD model, the test drug after 10 days of treatment significantly reduced colon weight, colon length, colon width, colon weight/length ratio and macroscopic score of colon. The test drug also showed decreased ulcer index and significant reduction in myeloperoxidase activity.

d) In-vivo model of *H. Pylori* infected rats with non steroidal anti inflammatory drug (NSAID hereinafter) induced ulcers is tested for the potential anti-*H. pylori* and anti-ulcer activity of the test drug. The test drug has showed dose dependent and time dependent reduction in the ulcer area along with complete eradication of *H. pylori* infection.

e) In a model of stress induced ulcers, histamine is administered to rats to induce ulcerative conditions and the effect of the test drug in preventing stress induced ulcer is confirmed by pretreating the animal with the test drug. The test drug is found effective in preventing histamine induced ulcers.

f) In a model of alcohol induced ulcers, ethanol is administered to rats that are pretreated with the test drug to induce ulcerative conditions. The test drug has showed prophylactic effect against ethanol induced ulcers.

The invention is further elaborated with the help of following examples. However, it is understood that these examples should not be construed to limit the scope of the invention.

EXAMPLES

Example-1

10 kilograms of *Centella asiatica* leaves were pulverized to 40 mesh size using hammer mill. The pulverized material was extracted with 50 liters of petroleum ether in a fixed bed counter current extractor repeatedly over a period of 8 hrs at 30° C. The extracted mass free of chlorophyll and fats was dried by circulating air into the bed. The dried mass is extracted with 75 liters of isopropyl alcohol at 30° C. for 8 hrs. The clear filtrate after extraction was concentrated under vacuum to get a paste. The paste was dissolved in 25 liters of demineralized water and filtered clear of insolubles. The clear water layer was extracted repeatedly and washed with methyl isobutyl ketone to get rid of all acidic material. This operation was monitored for absence of acidic components using TLC wherein TLC mobile phase was consisting of top layer of mixture n-butanol:ethyl acetate:water in the ratio of 4:1:5. The clear layer was passed through an adsorbent chromatographic column having vertical Column containing 250 ml of Amberlite® XAD-4 and washed with water to get rid of all adhering colours and particles. This was followed by elution cycle wherein the column was eluted with methyl alcohol and the solvent elute was concentrated under vacuum to get 500 gms powder. This powder was dissolved in 2500 ml of an aqueous alcohol comprising of 80% methyl alcohol and 20% water to get a clear solution. This solution was cooled to −15° C. to get asiaticoside crystals. The mass was filtered, water washed and dried at 80° C. The yield was 158 gms of asiaticoside having HPLC purity 99.6%

Example-2

10 kilograms of *Centella asiatica* leaves were pulverized to 40 mesh size using hammer mill. The pulverized material was extracted with 50 liters of petroleum ether in a fixed bed counter current extractor repeatedly over a period of 8 hrs at 30° C. The extracted mass free of chlorophyll and fats was dried by circulating air into the bed. The dried mass was extracted with 75 liters of 80% aqueous ethyl alcohol at 30° C. for 8 hrs. The clear filtrate, after extraction, was concentrated under vacuum to get a paste. The paste was dissolved in 25 liters of demineralized water and filtered clear of insolubles. The clear water layer was extracted repeatedly and washed with methyl isobutyl ketone to get rid of all acidic material. This operation was monitored for absence of acidic components using TLC wherein the TLC mobile phase was consisting of top layer of a mixture having n-butanol:ethyl acetate: water in the ratio of 4:1:5. The clear layer was passed through an adsorbent chromatographic column having vertical Column containing 250 ml of Amberlite® XAD-4 and washed with water to get rid of all adhering colours and particles. This was followed by elution cycle wherein the column was eluted with methyl alcohol and the solvent elute obtained is concentrated under vacuum to get 500 gms powder. The powder was dissolved in 2500 ml of an aqueous alcohol comprising of 80% methyl alcohol and 20% water to get a clear solution. This solution was cooled to −15° C. to get asiaticoside crystals. The mass was filtered, water washed and dried at 80° C. The yield obtained was 150 gms of asiaticoside having HPLC purity 99.2%

Example-3

10 kilograms of *Centella asiatica* leaves were pulverized to 40 mesh size using hammer mill. The pulverized material was extracted with 50 liters of petroleum ether in the fixed bed counter current extractor repeatedly over a period of 8 hrs at 30° C. The extracted mass free of chlorophyll and fats was dried by circulating air in to the bed. The dried mass was extracted with 75 liters of methyl alcohol at 30° C. for 8 hrs. The clear filtrate obtained after extraction was concentrated under vacuum to get a paste. The paste was dissolved in 25 liters of demineralized water and filtered clear of insolubles. The clear water layer was extracted repeatedly and washed with methyl isobutyl ketone to get rid of acidic material. The operation for absence of acidic components was monitored using TLC. The clear layer was passed through an adsorbent chromatographic column having vertical Column containing 250 ml of Amberlite® XAD-4 and washed with water to get rid of all adhering colours and particles. This was followed by an elution cycle wherein the column was eluted with methyl alcohol to obtain a solvent elute. The solvent elute is concentrated under vacuum to get 500 gms powder. This powder was dissolved in 2500 ml of an aqueous alcohol, comprising of 80% methyl alcohol and 20% water, to get a clear solution. This solution was cooled to −15° C. to get Asiaticoside crystals. The mass was filtered, water washed, and dried at 80° C. The yield obtained was 145 gms of Asiaticoside having HPLC purity 99.8%

Example-4

10 kilograms of *Centella asiatica* leaves were pulverized to 40 mesh size using hammer mill. The pulverized material was extracted with 50 liters of petroleum ether in a fixed bed counter current extractor repeatedly over a period of 8 hrs at 30° C. The extracted mass free of chlorophyll and fats was dried by circulating air into the bed. The dried mass is extracted with 75 liters of Isopropyl alcohol, containing 80% isopropyl alcohol and 20% water, at 30° C. for 8 hrs. The clear filtrate after extraction was concentrated under vacuum to get a paste. The paste was dissolved in 25 liters of demineralized water and filtered clear of insolubles. The clear water layer was extracted repeatedly and washed with methyl isobutyl ketone to get rid of all acidic material. This operation was monitored for absence of acidic components using TLC. The clear layer was passed through an adsorbent chromatographic column having vertical column containing 250 ml of Amberlite® XAD-4 and washed with water to get rid of all adhering colours and particles. This was followed by an elution cycle wherein the column was eluted with methyl alcohol and the solvent elute obtained is concentrated under vacuum to get 500 gms powder. The powder was dissolved in 2500 ml of an aqueous alcohol, comprising of 80% methyl alcohol and 20% water, to get a clear solution. The clear solution was cooled to −15° C. to get asiaticoside crystals. The asiaticoside mass was filtered, water washed and dried at 80° C. The yield was 158 gms of asiaticoside having HPLC purity 99.6%

Example-5

10 kilograms of *Centella asiatica* leaves were pulverized to 40 mesh size using a hammer mill. The pulverized material was extracted with 50 liters of petroleum ether in a fixed bed counter current extractor repeatedly over a period of 8 hrs at 30° C. The extracted mass free of chlorophyll and fats was dried by circulating air in to the bed. The dried mass is extracted with 75 liters of 70% isopropyl alcohol containing 30% water at 30° C. for 8 hrs. The clear filtrate after extraction was concentrated under vacuum to get a paste. The paste was dissolved in 25 liters of demineralized water and filtered clear of insolubles. The clear water layer was extracted repeatedly and washed with methyl isobutyl ketone to get rid of all acidic material. This operation was monitored for absence of acidic components using TLC. The clear layer was passed through an adsorbent chromatographic column having vertical column containing 250 ml of Amberlite® XAD-4 and washed with water to get rid of all adhering colours and particles. This was followed by elution cycle wherein the column was eluted with methyl alcohol and the solvent elute obtained is concentrated under vacuum to get 500 gms powder. This powder was dissolved in 2500 ml of an aqueous alcohol, comprising of 80% methyl alcohol and 20% water, to get a clear solution. The clear solution was cooled to −15° C. to get asiaticoside crystals. The mass was filtered, water washed and dried at 80° C. The yield obtained was 157 gms of asiaticoside having HPLC purity 99.8%.

Example-6

Availability of Test Drug at Site of Action

The Pharmacokinetic parameters of the test drug were studied in healthy rats to determine the bioavailability of the test drug.
Procedure: In this study, animals were fasted overnight before the experiment and were given a single oral dose of 250 mg/kg of test drug. The blood samples were collected at 0, 0.25, 0.50, 1, 2, 3, 4, 5 and 6 hours after dosing. Plasma was obtained by centrifugation of blood at 7000 rpm for 15 min at 4° C. and kept at −20° C. until analysis was carried out. The animals were kept in the metabolic cages for collection of urine and feces. A Reverse Phase HPLC method was developed for detection of the test drug in the plasma, urine and feces. Elimination of the test drug by urine and feces was determined at 0-4 hr, 4-8 hr and 8-24 hr.

Observation: It was observed that no drug was absorbed into the blood systemically even at the high dose of 250 mg/kg. This was reconfirmed by absence of asiaticoside in urine. It was observed that the test drug passes in an unchanged form through the gastro intestinal tract and completely excretes through the fecal matter. Further, it was observed that the test drug does not absorb into the blood that substantially increases the bioavailability of the asiaticoside composition at a diseased site. In the experiments conducted in this context, it was observed that about 81.42% of the drug was recovered from fecal matter. Hence, it was confirmed that there is a potential for the test drug in treatment of IBD and related diseases.

Example-7

Effect of Test Drug in TNBS Induced Colitis in Rats

The trinitrobenzenesulfonic acid (TNBS) induced colitis is one of the standard animal models used for IBD. In this model, a single intracolonic administration of TNBS damages the colonic epithelium and induces prolonged chronic inflammation. The transmural granulomatous inflammation of the colon is similar to histopathological features exhibited in Crohn's disease.

Procedure: In this study, Male Wistar rats (280-291 g) were fasted for 48 hrs, and put under anaesthesia. A 3 mm diameter cannula was inserted into the anus to the depth of 8 cm and 25 mg of TNBS dissolved in 0.25 ml of 30% ethanol solution was injected to each rat. The rats were positioned tail up for 1 minute. After 1 day, the test drug was administered orally once daily for 10 days. A healthy control group receiving only saline but no TNBS was maintained. On day 11, each group of rats were sacrificed by cervical dislocation and the colon was isolated for physical examination. Colon samples were preserved in 10% neutral formalin solution for histopathological evaluation.

Observations: In the performed experiments, TNBS induced IBD conditions such as increased colon weight, colon weight to length ratio and myeloperoxidase activity were reversed significantly by treatment with test drug for 10 days at a dose of 50 mg/kg (p.o.) once daily. The test drug also healed the lesions produced by TNBS as seen from the reduction in microscopic scores and colonic ulcer index. The reversal of myeloperoxidase activity by test drug confirmed its potential in healing colonic lesions seen in IBD.

TABLE 1

EFFECT OF TEST DRUG ON COLON WEIGHT AND LENGTH IN TNBS INDUCED IBD IN RATS AFTER 10 DAYS OF TREATMENT

|  | Healthy control | TNBS control | Test Drug |
| --- | --- | --- | --- |
| Colon weight (g) | $1.15 \pm 0.02$ | $2.22 \pm 0.1^{\#\#\#}$ | $1.71 \pm 0.07^{***}$ |
| Colon length (mm) | $17.2 \pm 0.53$ | $13.64 \pm 0.34^{\#\#\#}$ | $14.14 \pm 0.53$ |
| Colon width (mm) | $0.377 \pm 0.32$ | $0.99 \pm 0.88^{\#\#\#}$ | $0.73 \pm 0.13$ |
| Colon weight/length ratio | $0.00 \pm 0.00$ | $8.80 \pm 0.58^{\#\#\#}$ | $4.40 \pm 0.68^{**}$ |
| Myeloperoxidase activity (U/mg) | $0.01 \pm 0.0002$ | $0.05 \pm 0.0003^{\#\#\#}$ | $0.02 \pm 0.0003^{***}$ | n = 6;
For each of the parameters, data analyzed using One Way ANOVA followed by Dunnett test.
$^{\#\#\#}P < 0.001$, as compared to Healthy control group;
$^{*}P < 0.05$,
$^{**}P < 0.01$ and
$^{***}P < 0.001$ as compared to TNBS control group.

TABLE 2

EFFECT OF TEST DRUG ON COLON MICROSCOPIC SCORES IN TNBS INDUCED IBD IN RATS AFTER 10 DAYS OF TREATMENT

|  | Healthy control | TNBS control | Test Drug |
| --- | --- | --- | --- |
| Microscopic Score | $0.00 \pm 0.00$ | $8.80 \pm 0.58^{\#\#\#}$ | $4.40 \pm 0.68^{***}$ |
| Colon Ulcer Index | $0.00 \pm 0.00$ | $9.92 \pm 0.31^{\#\#\#}$ | $2.85 \pm 0.17^{***}$ | n = 6;
For each of the parameters, data analyzed using Kruskal Wallis followed by Dunns Multiple Comparison Test.
$^{\#\#\#}P < 0.001$, as compared to Healthy control group;
$^{*}P < 0.05$,
$^{**}P < 0.01$ and
$^{***}P < 0.001$ as compared to TNBS control group.

TABLE 3

EFFECT OF TEST DRUG ON BODY WEIGHT IN TNBS INDUCED IBD IN RATS AFTER 10 DAYS OF TREATMENT

| Days | Healthy control | TNBS control | Test Drug |
| --- | --- | --- | --- |
| Normal (Day −2) | $291.00 \pm 1.83$ | $280.33 \pm 2.62^{ns}$ | $286.50 \pm 3.14^{ns1}$ |
| Day 0 | $264.17 \pm 2.21$ | $250.00 \pm 2.00^{\#}$ | $252.67 \pm 3.121^{ns1}$ |
| Day 11 (10 days of treatment) | $296.33 \pm 1.45$ | $229.60 \pm 0.81^{\#\#\#}$ | $293.00 \pm 0.84^{***}$ | n = 6;
Data analyzed using Two Way ANOVA followed by Bonferroni post tests.
$^{\#}P < 0.05$,
$^{\#\#\#}P < 0.001$ as compared to Healthy control group;
$^{***}P < 0.001$ as compared to TNBS control group on respective day.
$^{ns}$-Not significant as compared with Healthy control;
$^{ns1}$-Not significant as compared with TNBS induced rats.

The effects of test drugs on TNBS induced IBD strongly indicated therapeutic value of test drug in treatment and management of IBD.

Example 8

Effect of Test Drug on Acetic Acid induced Colitis in Rats

The acetic-acid induced colitis is a model of IBD with a similarity of the inflammatory mediators to that of acute human intestinal inflammation.

Procedure: In this model, initial injury was an epithelial necrosis and edema that variably extended into the lamina propria, submucosa, or external muscle layers, depending of the concentrations and length of exposure to acetic acid. Male Wistar rats (280-291 g) were given the test drug once daily at dose of 50 mg/kg (p.o.) starting 72 h before induction of colitis. Rats were fasted for 24 hrs, anesthetized and a cannula that has 3 mm diameter was inserted into the anus to the depth of 8 cm for instilling 2 ml of 3% acetic acid into the colon for 30 s. After 24 hrs, animals were sacrificed by cervical dislocation, the colon was isolated and the parameters of colitis were measured.

Observations: Pre-treatment with the test drug in rats for 3 days had a significant reversal effect in acetic acid induced colitis symptoms. The reversal of acetic acid induced conditions such as increased colon weight and colon weight to length ratio, which indicated beneficial effects of test drugs on colitis. These effects were further confirmed by decrease in macroscopic lesion score and myeloperoxidase activity in colon tissues.

TABLE 4

EFFECT OF TEST DRUG ON COLON PARAMETERS IN ACETIC ACID INDUCED COLITIS IN RATS FOLLOWING PRETREATMENT FOR 3 DAYS

|  | Healthy control | Acetic acid control | Test Drug |
|---|---|---|---|
| Colon weight (g) | 1.11 ± 0.07 | 2.49 ± 0.14### | 1.53 ± 0.10*** |
| Colon length (mm) | 17.73 ± 0.18 | 13.55 ± 0.44### | 16.22 ± 0.63*** |
| Colon width (mm) | 0.40 ± 0.03 | 1.07 ± 0.06### | 0.71 ± 0.05*** |
| Colon weight/length ratio | 0.06 ± 0.0002 | 0.18 ± 0.006### | 0.09 ± 0.01*** |
| Myeloperoxidase activity (U/mg) | 0.01 ± 0.001 | 0.04 ± 0.006### | 0.02 ± 0.002** | n = 6;
For each of the parameters, data analyzed using One Way ANOVA followed by Dunnett test.
$P < 0.001$, as compared to Healthy control group;
***$P < 0.001$ as compared to Acetic Acid control group.

TABLE 5

EFFECT OF TEST DRUG ON COLON MICROSCOPIC SCORES IN ACETIC ACID INDUCED COLITIS IN RATS FOLLOWING PRETREATMENT FOR 3 DAYS

|  | Healthy control | Acetic Acid control | Test Drug |
|---|---|---|---|
| Microscopic score | 0.00 ± 0.00 | 9.33 ± 0.33### | 4.33 ± 0.71** |
| Colon ulcer Index | 0.00 ± 0.00 | 13.72 ± 0.48### | 4.34 ± 0.29*** | n = 6;
For each of the parameters, data analyzed using Kruskal Wallis followed by Dunns Multiple Comparison Test.
$P < 0.001$, as compared to Healthy control group;
**$P < 0.01$ and
***$P < 0.001$ as compared to Acetic Acid control group.

The effects of test drugs on acetic acid induced colitis strongly indicated therapeutic value of test drug in management of IBD.

Example 9

Effect of Test Drug on *H. Pylori* Infected Gastric Diseases

The effect of test drug on eradication of *H. Pylori* was tested in NSAID induced ulcers in rats after chronic administration for 9 weeks. *H. Pylori* infection was monitored by Polymerase Chain Reaction (PCR) and Rapid Urease Test (RUT) to validate the chronic treatment.
Procedure: Male Wistar rats (200-230 g) were fasted for 24 hrs and given Naproxen at a dose of 30 mg/kg (p.o.) for 3 consecutive days. After 24 hrs, brucella broth solution of viable *H. pylori* (ATCC 26695, strain MS-5, $10^8$ CFU) was administered (1 ml/animal) consecutively for 3 days. After 1 week, the test drug was administered at doses of either 120 mg/kg (p.o.) twice daily or 240 mg/kg (p.o.) once daily or 360 mg/kg (p.o.) once daily. The animals were sacrificed on completion of 9 weeks of treatment. Stomach of the sacrificed animal was isolated, gastric mucosa washed with saline and the pylorus was dissected for RUT. Mucosa was scrapped for myeloperoxidase estimation and DNA was amplified by PCR, gel electrophoresis for two non mutating genes 16S rRNA and hrgA.

Observations: The infection status was monitored in the stomach of rats by RUT and PCR amplification of two *H. pylori* genes after 4, 6 and 9 weeks of treatment. It was observed that the test drug at a dose of 360 mg/kg (p.o.) shows rapid antibacterial action on $3^{rd}$ week and subsequent eradication of *H. Pylori* infection in 9 weeks. However, the test drug administered at lower doses of 120 mg/kg (p.o.) twice daily and 240 mg/kg (p.o.) once daily was not effective in *H. Pylori* eradication. The effect of the test drug strongly indicated a therapeutic value in eradication of *H. Pylori* infection at high doses and also provided a pharmacological credence to the therapeutic potential for treatment of *H. Pylori* related gastric diseases and gastric carcinomas.

Example 10

Prophylactic Effect of Test Drug on Drug Induced Gastric Diseases

Gastric lesions induced by NSAIDS drugs such as Naproxen can aggravate inflammatory reactions in the GI tract. The potential of the test drug in preventing drug induced gastric lesions was studied in animal models of Naproxen induced ulcers.

Procedure: Male Wistar rats (220-230 g) were pretreated with the test drug at doses of either 30 mg/kg (p.o.) or 60 mg/kg (p.o.) or 120 mg/kg (p.o.) and then Naproxen was administered at a dose of 30 mg/kg (p.o.). The formation of ulcer and area of ulceration were compared with the Naproxen control group that did not undergo pretreatment with the test drug.

Observations: It was observed that pretreatment with the test drug prevented ulcer formation in a dose dependent manner. The highest dose of 120 mg/kg was found to be most effective in protecting against ulcerogenic action of Naproxen. Accordingly, the test showed potential prophylactic effect against ulcerogenic action of drugs.

TABLE 6

PROPHYLACTIC EFFECT OF TEST
DRUG ON NAPROXEN INDUCED
GASTRIC DISEASES IN RATS

| | Area of Ulceration (mm$^2$) |
|---|---|
| Naproxen Control | 5.50 ± 0.158 |
| Test Drug (30 mg/kg) + Naproxen | 5.49 ± 0.212$^{ns}$ |
| Test Drug (60 mg/kg) + Naproxen | 4.52 ± 0.169** |
| Test Drug (120 mg/kg) + Naproxen | 2.632 ± 0.146*** | n = 6;
Data analyzed using One Way ANOVA followed by Dunnett's Multiple Comparison test.
ns - Not significant;
**P < 0.01,
***P < 0.001 as compared to Naproxen control group.

Example 11

Prophylactic Effect of Test Drug on Stress Induced Gastric Diseases

Stress induced gastric lesion is a condition that can cause or aggravate inflammatory reactions in the GI tract. The potential of the test drug in preventing stress induced gastric lesions was studied in the animal models of histamine induced ulcers.
Procedure: Male Wistar rats (220-230 g) were pretreated with the test drug at the doses of either 30 mg/kg (p.o.) or 60 mg/kg (p.o.) or 120 mg/kg (p.o.) and then Histamine was administered at a dose of 300 mg/kg (i.p.). The formation of ulcer and area of ulceration were compared with a control group which did not undergo pretreatment with test drug.
Observations: It was observed that pretreatment with the test drug prevented the ulcer formation in a dose dependent manner. The highest dose of 120 mg/kg was most effective in protecting against ulcerogenic action of Histamine. Hence, it was confirmed that the test drug has potential prophylactic effect against stress induced ulcers.

TABLE 7

PROPHYLACTIC EFFECT OF TEST
DRUG ON HISTAMINE INDUCED
GASTRIC DISEASES IN RATS

| | Area of Ulceration (mm$^2$) |
|---|---|
| Histamine Control | 10.66 ± 0.1302 |
| Test Drug (30 mg/kg) + Naproxen | 9.242 ± 0.415* |
| Test Drug (60 mg/kg) + Naproxen | 7.062 ± 0.362*** |
| Test Drug (120 mg/kg) + Naproxen | 4.598 ± 0.323*** | n = 6;
Data analyzed using One Way ANOVA followed by Dunnett's Multiple Comparison test.
*P < 0.05,
***P < 0.001 as compared to Histamine control group.

Example 12

Prophylactic Effect of Test Drug on Alcohol Induced Gastric Diseases in Rat

Consumption of alcohol is another major factor resulting in gastric lesions. Accordingly, the potential of the test drug in preventing ethanol induced ulcers in animals was studied.
Procedure: Male Wistar rats were pretreated with the test drug at doses of either 30 mg/kg (p.o.) or 60 mg/kg (p.o.) or 120 mg/kg (p.o.) and then Ethanol was administered at a dose of 8 ml/kg (p.o.). The formation of ulcer and area of ulceration were compared with a control group which did not undergo pretreatment with the test drug. The mean ulcer area in this study was measured to be 174.4 mm$^2$±5.814 mm$^2$ in the control group indicating the ulcerogenic effect of ethanol.
Observations: It was observed that pretreatment with the test drug has prevented ulcers formation in a dose dependent manner. The highest dose of 120 mg/kg was most effective in protecting against ulcerogenic action of Ethanol. Accordingly, the significant prophylactic effect of the test drug against ulcers induced by alcohol consumption was confirmed.

TABLE 8

PROPHYLACTIC EFFECT OF TEST
DRUG ON ETHANOL INDUCED
GASTRIC DISEASES IN RATS

| | Area of Ulceration (mm$^2$) |
|---|---|
| Ethanol Control | 174.4 ± 5.814 |
| Test Drug (30 mg/kg) + Naproxen | 159.3 ± 4.846* |
| Test Drug (60 mg/kg) + Naproxen | 137.6 ± 4.069*** |
| Test Drug (120 mg/kg) + Naproxen | 110.4 ± 2.305*** | n = 6;
Data analyzed using One Way ANOVA followed by Dunnett's Multiple Comparison test.
*P < 0.05,
***P < 0.001 as compared to Ethanol control group.

Example 13

Effect of Test Drug in Treatment of IBD in Humans

A prospective study to assess the efficacy of the test drug in patients with IBD was conducted.
Procedure: In this study, three patients suffering from chronic symptoms of inflammatory bowel disease were given the test drug at a dose of 300 mg twice daily for a period of 6 months. Thereafter, the efficacy of the test drug was analyzed on the basis of patient reported outcome taken at the beginning and end of the study period.
Observations: It was observed that all patients were experiencing relief from IBD related symptoms such as abdominal pain, diarrhea, rectal bleeding, fever, nausea and vomiting. It was further observed that there was significant improvement in bowel control which was seen from reduced frequency of visits to restrooms, dependence on diarrhoea medication and pain associated with bowel movement. It was further observed that there were no incidences of joint pain, skin diseases or eye related complications. It was further observed that the test drug was well tolerated and showed efficacy in treatment of IBD.

TABLE 9

EFFECT OF TEST DRUG IN TREATMENT OF IBD IN HUMANS FOR 6 MONTHS

| | Patient Recorded Outcome† | | | | | |
|---|---|---|---|---|---|---|
| | Patient 1 | | Patient 2 | | Patient 3 | |
| Symptoms | Before | After | Before | After | Before | After |
| Abdominal pain | 3 | 1 | 3 | 0 | 3 | 1 |
| Diarrhea | 3 | 0 | 3 | 0 | 3 | 2 |
| Bleeding | 3 | 0 | 3 | 0 | 3 | 0 |
| Frequent trips to the bathroom | 3 | 0 | 3 | 1 | 3 | 0 |
| Dependence on medication diarrhea and pain | 3 | 0 | 3 | 0 | 3 | 1 |

†Scale of Severity of IBD symptoms (0—Absence; 1—Mild; 2—Moderate; 3—Severe)

Example 14

Effect on Test Drug in Treatment of Hemorrhoids in Humans

A prospective uncontrolled pilot study to access the efficacy of the test drug in patients with hemorrhoids was conducted.

Procedure: In this study, five patients suffering from chronic haemorrhoid symptoms of rectal bleeding, pain during defecation and rectal irritation were given the test drug at a dose of 300 mg twice daily for 15 days. The efficacy of the test drug was analyzed on the basis of patient reported outcome taken at the beginning and end of the study period.

Observations: It was observed that the test drug had an efficacy in providing immediate relief from symptoms of Haemorrhoids and anal fissures. It was further observed that all patients were relieved of rectal bleeding on the $3^{rd}$ day of treatment with the test drug. It was further observed that there was significant relief in pain and irritation associated with bowel movement by the end of the treatment period.

TABLE 10

EFFECT OF TEST DRUG IN TREATMENT OF HEMORRHOIDS IN HUMANS FOR 15 DAYS

| Symptoms | Median Value of Patient Reported Outcome† (n = 5) | |
|---|---|---|
| | Before Treatment | After Treatment |
| Pain | 5 | 2 |
| Edema | 3 | 1 |
| Itching | 5 | 2 |
| Bloody stool | 5 | 0 |
| Difficulty to sit or walk | 5 | 1 |

†Scale of assessment (0 - Absence to 5 - Severe)

The present invention has been described in an illustrative manner, and it is to be understood that the terminology used is intended to be in the nature of description rather than of limitation.

It is not intended to be exhaustive or to limit the invention to the precise form disclosed. Many modifications and verifications are possible in light of the above teaching. It is intended that the scope of the invention be limited not by this detailed description, but rather by the claims appended hereto. It is also to be understood that the following claims are intended to cover all of the generic and specific features of the invention described herein.

We claim:

1. A process to obtain asiaticoside of at least 99% purity, said process consisting of:
   a) treating pulverized source material of asiaticoside with a first solvent;
   b) extracting the treated pulverized material with a second solvent to obtain an extract or filtrate;
   c) distilling and dissolving the extract or the filtrate in demineralized water followed by washing in a third solvent to obtain a solution;
   d) passing the solution through adsorbent and eluting with an alcoholic solvent to obtain a solvent elute;
   e) vacuum concentrating the solvent elute to obtain a powder of asiaticoside;
   f) dissolving the powder in alcohol and crystallizing to obtain the asiaticoside of at least 99% purity.

2. A process of preparing a pharmaceutical composition comprising asiaticoside of at least 99% purity along with pharmaceutically acceptable excipient(s), said process consisting of:
   a) treating pulverized source material of asiaticoside with a first solvent;
   b) extracting the treated pulverized material with a second solvent to obtain an extract or filtrate;
   c) distilling and dissolving the extract or the filtrate in demineralized water followed by washing in a third solvent to obtain a solution;
   d) passing the solution through adsorbents and eluting with an alcoholic solvent to obtain a solvent elute;
   e) vacuum concentrating the solvent elute to obtain a powder of asiaticoside;
   f) dissolving the powder in alcohol and crystallizing to obtain asiaticoside;
   g) adding the pharmaceutically acceptable excipient(s) to the asiaticoside to obtain the pharmaceutical composition comprising asiaticoside of at least 99% purity; and
   f) optionally formulating said composition into tablets, troches, lozenges, aqueous or oily suspensions, ointments, patches, gels, lotions, dentifrices, capsules, emulsions, creams, sprays, drops, dispersible powders or granules, emulsions in hard or soft gel capsules, syrups, elixirs, phytoceuticals, nutraceuticals and food stuffs or any combination thereof.

3. The process as claimed in claim 1 or claim 2, wherein said source material of asiaticoside is selected from the group comprising plants and animals.

4. The process as claimed in claim 3, wherein said plant source is *Centella asiatica*.

5. The process as claimed in claim 1 or claim 2, wherein said extracting is carried out at a temperature ranging from about 20° C. to about 30° C., at a time period of about 8 hours to about 24 hours.

6. The process as claimed in claim 1 or claim 2, wherein said first solvent is selected from the group comprising aliphatic compounds, ketones, alcohols, nitriles, esters, ethers or any combination thereof.

7. The process as claimed in claim 1 or claim 2, wherein said second solvent is an aliphatic alcohol selected from the group comprising methyl alcohol, ethyl alcohol, propyl alcohol, isopropyl alcohol and butyl alcohol either alone or in combination with water in a ratio ranging from about 60% to about 99%.

8. The process as claimed in claim 1 or claim 2, wherein said third solvent is selected from the group comprising hexane, methyl isobutyl ketone and petroleum ether or any combination thereof.

9. The process as claimed in claim 1 or claim 2, wherein said adsorbent is a resin bed.

10. The process as claimed in claim 1 or claim 2, wherein said alcoholic solvent has carbon atom ranging from C-1 to C-4 selected from the group comprising methanol and isopropyl alcohol or any combination thereof.

11. The process as claimed in claim 1 or claim 2, wherein said vacuum concentrating is carried out at a temperature ranging from about 50° C. to about 65° C.

12. The process as claimed in claim 1 or claim 2, wherein said alcohol is selected from the group comprising ethyl alcohol, methyl alcohol, isopropyl alcohol and any combination thereof.

13. The process as claimed in claim 1 or claim 2, wherein said crystallizing is carried out at a temperature ranging from about −15° C. to about 0° C.

14. The process as claimed in claim 6, wherein said first solvent is petroleum ether or methyl isobutyl ketone.

\* \* \* \* \*